United States Patent [19]

Caloyannis et al.

[11] Patent Number: 4,843,231

[45] Date of Patent: Jun. 27, 1989

[54] APPARATUS FOR THE INSPECTION OF TRANSPARENT MATERIALS UTILIZING A DIFFUSING SCREEN

[75] Inventors: Theodore Caloyannis, Courbevoie; Pierre Lamborot, Paris, both of France

[73] Assignee: Saint-Gobain Cinematique et Controle, Gennevilliers, France

[21] Appl. No.: 279,325

[22] Filed: Dec. 2, 1988

Related U.S. Application Data

[63] Continuation of Ser. No. 76,518, Jul. 22, 1987, abandoned.

[30] Foreign Application Priority Data

Jul. 28, 1986 [FR] France .................................. 86 10900

[51] Int. Cl.[4] ............................................. G01N 21/90
[52] U.S. Cl. .................................. 250/223 B; 356/240; 356/428
[58] Field of Search ............................ 250/223 B, 224; 356/239, 240, 428; 209/526

[56] References Cited

U.S. PATENT DOCUMENTS 3,987,301 10/1976 O'Connor .......................... 250/227
4,338,028 7/1982 Tailleur et al. ................. 250/223 B
4,584,469 4/1986 Loualanti ........................ 250/223 B

FOREIGN PATENT DOCUMENTS 0186278 7/1986 European Pat. Off. .
3145686 5/1983 Fed. Rep. of Germany .
0042093 4/1978 Japan ................................ 356/240

OTHER PUBLICATIONS

Sanders, "Solid State Optics for Sidewall and Dimensional Inspection of Glassware", 22 Glass Technology (Jun. 1981), p. 139.

Primary Examiner—Edward P. Westin
Attorney, Agent, or Firm—Pennie & Edmonds

[57] ABSTRACT

The invention relates to an apparatus for the optical inspection of partially transparent articles. The apparatus comprises means for transporting the body to the inspection station and orienting it therein which comprises a horizontal plate having a vertical axis which is driven by a star wheel carrying rollers which permit rotation of the object at the inspection station by an exterior counter roller. The device further comprises a translucent diffusing screen; a receiver having a linear camera for observing the rear surface of the screen; and a fixed light emitter arranged outside the mounting of the body.

12 Claims, 3 Drawing Sheets

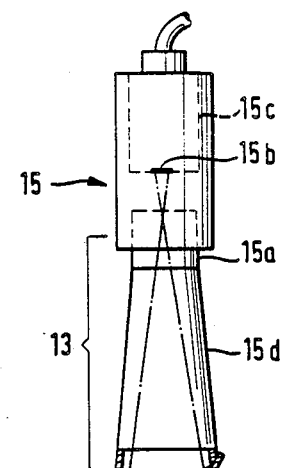
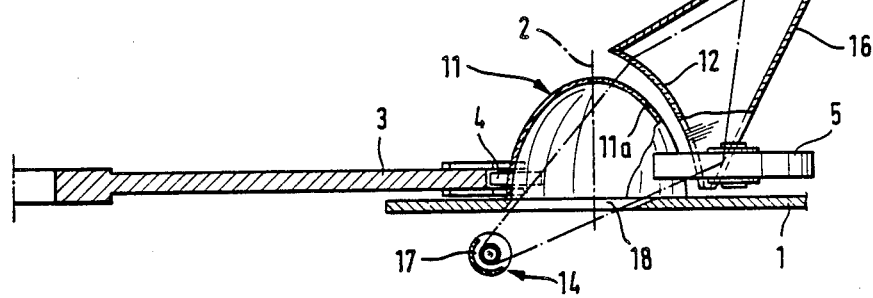
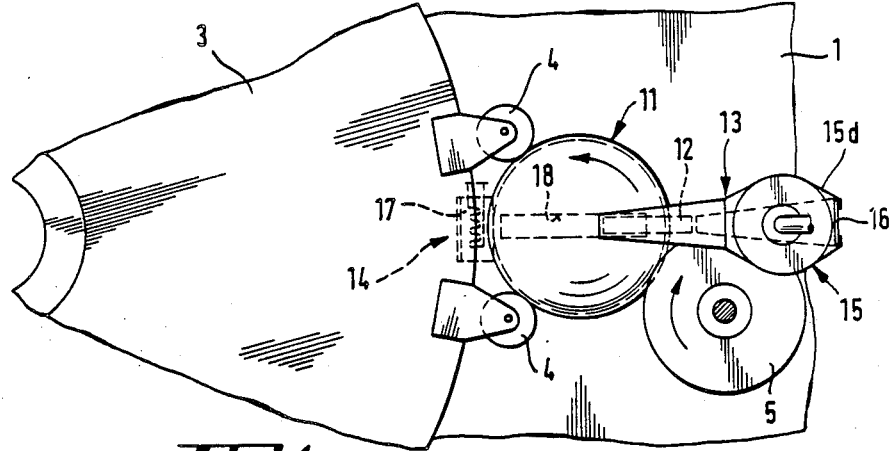

APPARATUS FOR THE INSPECTION OF TRANSPARENT MATERIALS UTILIZING A DIFFUSING SCREEN

This is a continuation, of application Ser. No. 076,518, filed July 22, 1987.

FIELD OF THE INVENTION

The invention relates to the optical inspection of bodies which are partially transparent.

DESCRIPTION OF THE PRIOR ART

Modern methods for the optical inspection of bodies having partial transparency rely upon the electronic analysis of the signal fluctuations or perturbations which are retransmitted, section by section, by the body to be inspected, from a suitable light source. These methods are used for inspecting articles having at least a partial axial symmetry, particularly glass articles, such as bottles or drinking glasses, or articles formed from plastic materials.

An analysis of the values thus obtained is then carried out as a function of the different criteria used in reviewing the results for each object. These results demonstrate the position, extent and magnitude of each fault in the body of the inspected article. As a general rule, however, neither the method of analysis nor the method of synthesis chosen depends directly on the observation method. Thus they are not within the subject of the present invention and will not be further described herein.

A major difficulty arises, however, in obtaining a strong enough signal. When covering fairly large regions of the articles to be inspected, the operation is normally carried out by traversing, column by column, and analyzing, more or less finely, parallel to the axis, successive bands of the chosen amplitude. The optical devices which have previously been utilized for this purpose, however, have met with little success.

In these prior art devices, rather than observing the wall of the article directly, or the image that the object produces of the light source, the light beam projected by transparency is directly intercepted by means of a suitably sized receiver situated in a relatively close flat plane. The receiver comprises a network of detectors in form of a rectangular matrix, masked by a translucent diffusing screen. The screen permits the maximum amount of light to be gathered while allowing this light to be transmitted to detectors independently of the direction of the rays striking it.

In some instances, the light passes through the body only once. The image observed thus constitutes to some extent the shadow of the zone of the wall closest to the translucent screen. However, most frequently, the light passes through the object twice and the image thus reflected shows up certain faults in the far wall thereof.

With the use of the above-described prior art devices, it is generally preferred, in particular for articles which may be revolved, to operate by rotating the object through one complete revolution at a fixed station or, with the use of a follower, along successive principal meridians or generators. The description which follows refers particularly to this type of inspection. It is, however, possible in certain cases to operate only using a translational passage mode wherein the object is inspected at at least one, but preferably at a plurality of complementary angles. When the article is observed at only one angle, there is obtained a less detailed but more rapid analysis which is sufficient in many cases since the transposition is immediate.

Those portions of the apparatus utilized to present the articles at the inspection station and rotating them thereupon are usually associated with a horizontal reference plate. The optical members of the apparatus are normally arranged along a single plane of symmetry at the inspection station, perpendicular to the path of passage therethrough. The devices most commonly employed for this purpose use plate transporters or drum transporters having a vertical axis. The symmetrical plane will thus be a vertical plane passing through the axis of the apparatus.

In particular, apart from members well known in the art for presenting the body to be inspected at the inspection station, a prior art device, which is described in DE-A-3145686 comprises, in the principal plane of symmetry of the inspection station:

a receiver combining a rectilinear line of closely spaced photosensitive elements arranged vertically so as to face the position of the body and having a flat translucent diffusing screen placed along its front surface; and at a location removed from the mounted body, a fixed light emitter generating a laser light beam along said plane of symmetry, which is narrow but which spreads to form a fan shape or ribbon adapted to illuminate on the screen, in a sufficiently homogeneous manner, a narrow zone covering at least one segment of objects selected for examination.

In the device described above and in comparable devices the screen is necessarily placed close to the network of detectors, at a distance on the same order as the mesh of the latter, so that each detector element is illuminated by the single zone of the screen which faces it. In order to better isolate each cell, it has been suggested to interpose a grid or honeycomb. This arrangement becomes inefficient when it is desired, as proposed in the German application discussed above, to obtain a precise analysis using a mesh on the order of one millimeter since it leads to an excessive loss of light, among other disadvantages. Its use also becomes pointless if continuous strips of photodiodes are used since their sensitive areas occupy almost the whole of the surface.

SUMMARY OF THE INVENTION

According to the present invention, the diffusing screen is arranged in the immediate vicinity of the object, as close thereto as is reasonably possible. It avoids the path of travel of the object during its movement when this one is mounted upon the device and subsequently removed. Further, the line of photosensitive elements is formed in the apparatus of the invention by a continuous strip of diodes of a linear camera placed at a distance from the object. The objective of this camera faces the screen, on which it is focused with a desired depth of field.

Thus, taking advantage of principles well known in the art and by separating the two portions of the apparatus, the invention permits the user to readily obtain a finer image of the body to be inspected. The diffusing screen may easily be designed to follow the profile of the object closely and it may be interchangeable, in particular for use with bodies having different configurations.

It is also possible, for reasons of convenience such as bulkiness, but also to improve the sensitivity, to obliquely arrange the different optical members relative to the plane of symmetry.

In practice, a receiver of a type known in the art, a camera having a known type of objective and a photosensitive member formed by a simple straight strip of diodes, preferably orientable, is suitable for fine observation of the image provided by the combination of regions to be examined. Advantageously, the device may also be provided with a return mirror allowing it to be oriented so as to be able to place it at the desired observation distance to permit it to cover the whole height to be inspected without creating excessive lateral bulk.

The diffusing screen may be thin, translucent flat plate, formed of a sheet of opal material or glass which is frosted on its front face. If necessary, the screen may also be comprised of a juxtaposition of surfaces oriented according to a prismatic arrangement along the profile of the object's path. The screen may further be provided with a curved surface, such as a right section or a slightly oblique section, which may or may not be vertical, of a cylinder having an axis perpendicular to the plane of symmetry.

Thus the screen would follow the shape of the article, which preferably will be at a distance of from about 0.3 to 1 centimeter from the screen. This distance must remain sufficiently constant without creating a sinuosity which is excessive since this would create difficulties, either in the construction of the apparatus or in the observation of the object with regard to angles of illumination or observation or possibly with regard to the depth of field attainable with the device. The thinner the screen, the finer and more sensitive the analysis will be.

With regard to the emitter, this member may comprise a simple concentrated light source, diaphragmed or anamorphosed as a narrow beam. However, a projector is preferably used, having an optical system with a point or linear source. This source emits a narrow beam which is diaphragmed in principle to a flat beam so as to illuminate the segments of the body chosen for examination. This beam passes through the article's axis of symmetry or it at least passes in the close vicinity thereof, if required, in order to allow the screen to retransmit towards the receiver a sufficiently uniform light flux. It is possible to utilize a number of these projectors, each illuminating a section of the object at an adjustable intensity in order to cover successive areas of illumination and to generate a uniform light field or possibly to correct the influence of angular differences. This emitter may also be provided with an optical return system.

As indicated above, a feature of the invention is that the optical members may be positioned away from the plane of symmetry, that is, the adjustable receiver and emitter may be focused on the diffusing screen by flat observation means and illumination means corresponding to principal planes which are adjacent but different, one and the other in principle being parallel to the axis of the article in position for inspection or slightly inclined to it.

BRIEF DESCRIPTION OF THE DRAWINGS

FIGS. 1 and 2, respectively, in plan and in elevation, show an inspection carried out in an axial plane;

DETAILED DISCUSSION OF THE PREFERRED EMBODIMENTS

Figure 4:
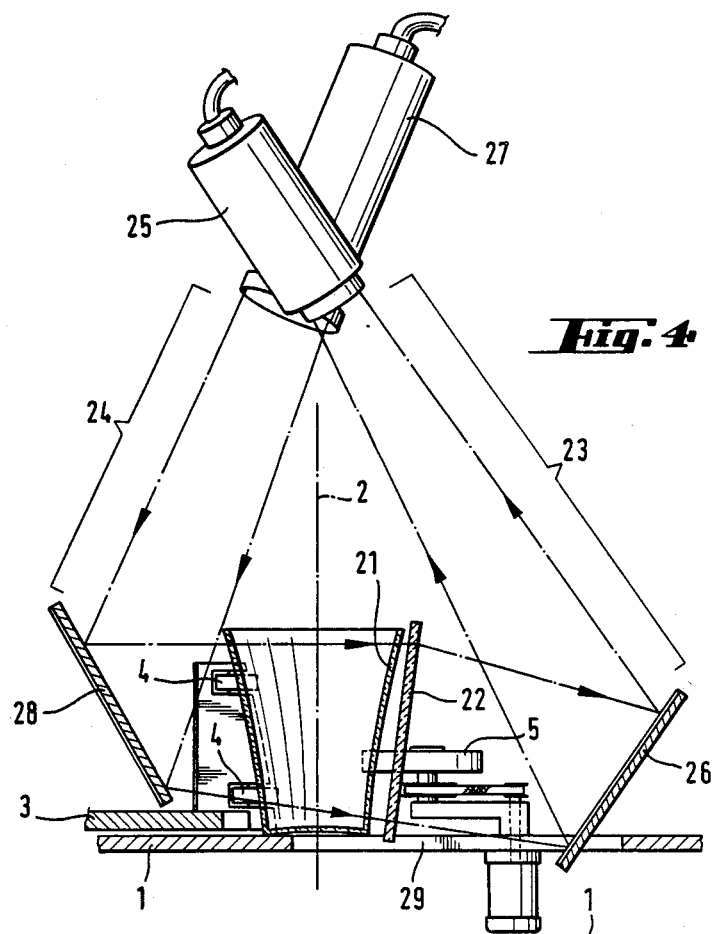
FIGS. 3 and 4, respectively, in plan and in elevation, show the same inspection being carried out in a slightly different mode.

Two examples of inspection of glass will now be described in greater detail with reference to the drawings discussed above.

The device is mounted on an apparatus of known type with the article resting on horizontal plate 1. Axis 2 is thus vertical and is driven by star wheel 3 carrying rollers 4. Rollers 4 allow exterior counter-roller 5 to rotate the article at the inspection station. This is a common type of arrangement which has been chosen for convenience and it will therefore not be described in any further detail.

The first example, as shown in FIGS. 1 and 2, corresponds to an inspection of cup 11 having an ellipsoidal shape similar to that of a wine glass. An edge of cup 11 rests on plate 1. The whole of the apparatus is arranged along the plane of FIG. 2 which passes through the axis of star wheel 3. Screen 12, receiver 13 and emitter 14 are symmetrical with respect to this plane.

Screen 12, formed of a narrow, thin plate of translucent opal or plastic material which is cylindrically curved, is arranged transversely to the plane of symmetry, along the principal generator or exterior meridian 11a of the article in the inspection position, without, however, following its curve exactly.

Receiver 13 comprises camera 15 of which objective 15a is placed in front of rectangular line 15b of photosensitive diodes connected to preamplifier 15c. This assembly is inside casing 15d which contains return mirror 16 which, when it is directed towards the rear surface of the screen, allows the objective to be vertically oriented. This reduces the horizontal bulk of the apparatus and, by focusing the object on this screen, defines there (in the plane of FIG. 2) a segment for examination which extends from the edge to near the apex of the cup.

Emitter 14 is formed from lamp 17 which is provided with a reflector. It is placed inside the device below the reference plate. Straight slot 18 diaphragms the light from the emitter into a thin beam. This beam forms on the screen, astride the median plane, a luminous zone which covers the segment to be examined. In the presence of an article within the beam, only one wall is traversed. Possible faults in the glass will be shown as local variations in illumination. These variations, when detected by the apparatus, will indicate faults and, if required, a moveable member having a suitable time lag may be utilized for subsequent removal of the article.

Figure 3:
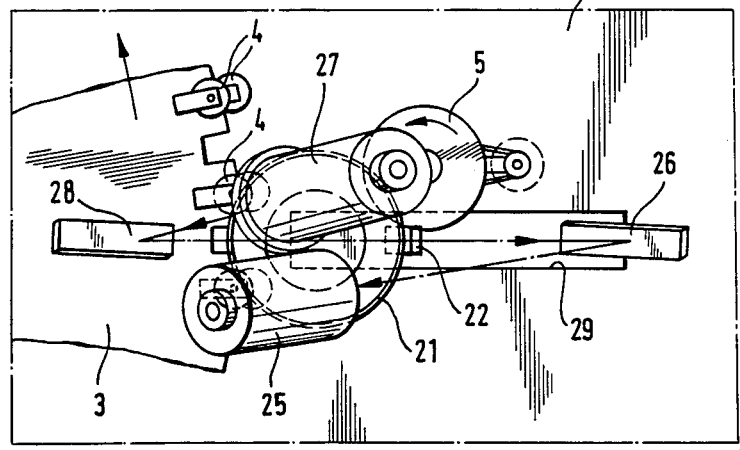

The second example, shown in FIGS. 3 and 4, relates to the inspection of glass 21 having a generally trunconic shape with a slight curvature of the principal generators when placed upright.

In such a situation, the translucent screen is a flat glass plate 22 frosted on its forward surface, i.e., that surface which is directed toward the article. It is located fairly close to the corresponding principal generator and perpendicular to the plane of FIG. 4.

With respect to the plane of FIG. 4, which passes through the axis of star wheel 3, the apparatus is not totally symmetrical. Receiver 23 and emitter 24 are, in effect, placed side by side above the path of the article.

Further, receiver 23, which is similar to receiver 13, has its camera 25 directed downwardly toward return mirror 26. Mirror 26 is inclined at an angle of about 40° to the vertical, as shown in FIG. 3, in a very slightly oblique transverse orientation. This permits focusing it on the screen along the closest generator by suitably arranging the line of diodes.

Emitter 24 comprises projector 27 which is directed downwardly toward narrow return mirror 28 which is also slightly displaced. It is inclined at about 40° to the vertical in order to return the beam illuminating the screen in a slightly downward direction. As for the receiver, this arrangement permits the projector to be located at a sufficient distance from the object without excessive horizontal bulk, the beam passing successively through the two walls to illuminate, in a narrow zone, the whole of the height of the second between them while avoiding the upper edges, which are sources of parasite signals.

Slit 29 is formed in plate 1 to permit the passage of light rays therethrough.

Figure 5:
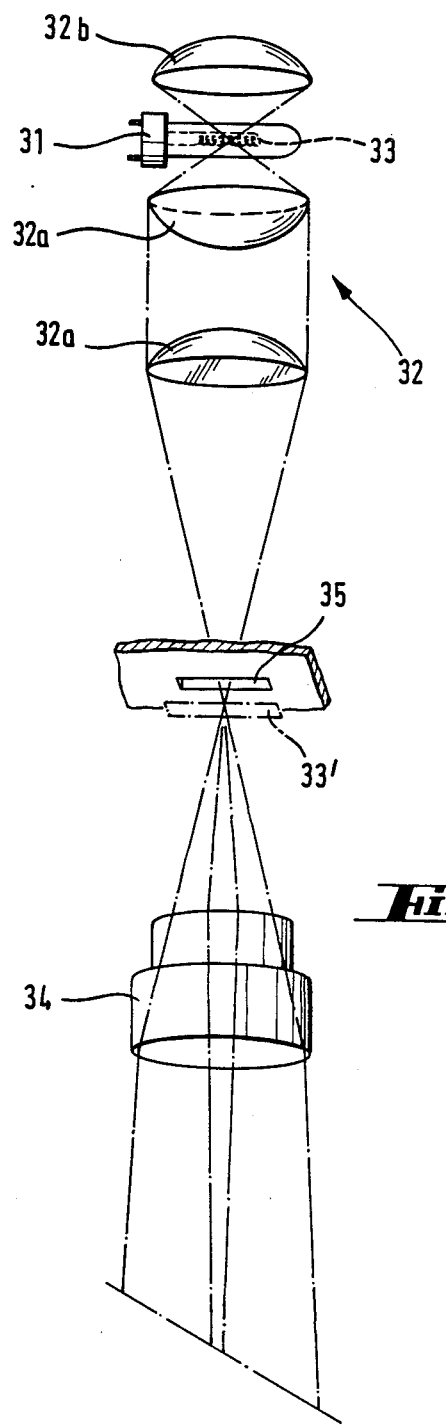
FIG. 5 is a schematic view illustrating in detail the projector used in the inspection depicted in FIGS. 3 and 4.

As shown in FIG. 5, the projector, of a type known in the art, utilizes lamp 31 and condenser 32, formed of two lenses 32a, associated with a concave mirror 32b, to form the image 33' of its filament 33 nearby. This light is recovered by objective 34.

Since this projector is not a point source, mirror 28, despite its narrow shape, does not perfectly diaphragm the beam emitted by the projector to a flat beam. This is why objective 34 must be adjusted with a field diaphragm having slit 35, with dimensions of 0.7 mm by 15 mm, for example. This diaphragm may be placed in the neighborhood of image 33' but slightly defocused so that a narrow rectangular image is formed in the region of screen 22 when the body is not positioned within the light path. This image is fifteen to twenty times larger than the object and of practically homogeneous luminosity. It should be noted that it would also be possible to study the bottom of the article in the same manner.

In the oblique arrangement described above, wherein the planes upon which the principal sections of the object lie are different, even though they cross in the vicinity of the screen, it is not difficult to place the receiver outside of the direct field of the emitter. This improves the ability of the screen to diffuse the image, thus improving the sensitivity of the apparatus and also reducing dazzling.

While it is apparent that the invention herein disclosed is well calculated to fulfill the objectives stated above, it will be appreciated that numerous modifications and embodiments may be devised by those skilled in the art, and it is intended that the appended claims cover all such modifications and embodiments as fall within the true spirit and scope of the present invention.

We claim:

1. An apparatus for the optical inspection of transparent bodies which comprises:
   (a) a means for transporting said bodies to an inspection station located upon said apparatus;
   (b) a means for rotating said bodies at the inspection station;
   (c) a fixed light emitter placed at a distance from said body and used for generating a narrow light beam which is capable of passing through a narrow zone of said transparent body;
   (d) a narrow translucent diffusing screen mounted on said apparatus and situated in the immediate vicinity of said transparent body, said screen having a front and a back, the front of said screen being illuminated by the narrow light beam from the emitter after said beam passes through the transparent body; and
   (e) a receiver comprising an objective lens and a line of photosensitive elements formed by a continuous strip of diodes wherein said receiver is placed at a distance from the transparent body and the objective lens faces the back of said screen and is located so that an image of the back of said screen is in focus at the line of photosensitive elements.

2. The inspection apparatus of claim 1, wherein said strip of diodes is rectilinear but orientable.

3. The inspection apparatus of claim 1, wherein said translucent screen has a curved surface extending along a profile of a path located upon said apparatus along which said body is transported.

4. The inspection apparatus of claim 1, wherein said emitter comprises a projector having an optical system using a light source for emitting a narrow beam which is diaphragmed to a flat beam passing through an axis of symmetry of each said body.

5. The inspection apparatus of claim 1 wherein at least one of said receiver and said emitter is provided with at least one return mirror.

6. The inspection apparatus of claim 1, wherein said receiver and said emitter are arranged obliquely.

7. The inspection apparatus of claim 6 wherein said receiver is positioned outside of a direct field covered by said emitter.

8. The inspection apparatus of claim 7, wherein said emitter and said receiver are positioned in planes of different principal sections, said planes being adjacent a plane of symmetry for an inspection station of said apparatus.

9. The inspection apparatus of claim 1, wherein said emitter comprises a projector having an optical system using a light source for emitting a narrow beam which is diaphragmed to a flat beam, said beam passing at least adjacent to an axis of symmetry of each said body.

10. The inspection apparatus of claim 9, wherein said light source is a linear source.

11. The inspection apparatus of claim 9, wherein said light source is a point source.

12. An apparatus for the optical inspection of transparent bodies which comprises:
   (a) a means for transporting said bodies to an inspection station located upon said apparatus;
   (b) a means for rotating said bodies at the inspection station;
   (c) a fixed light emitter placed at a distance from said body and used for generating a narrow light beam which is capable of passing through a narrow zone of said transparent body;
   (d) a narrow translucent diffusing screen mounted on said apparatus and situated uniformly proximate to an inspection surface of said transparent body, said screen having a front and a back, the front of said screen being illuminated by the narrow light beam from the emitter after said beam passes through the transparent body; and
   (e) a receiver comprising an objective lens and a line of photosensitive elements formed by a continuous strip of diodes wherein said receiver is placed at a distance from the transparent body and the objective lens faces the back of said screen, and is located so that an image of the back of said screen is in focus at the line of photosensitive elements.

* * * * *